United States Patent [19]

Weischer et al.

[11] Patent Number: 5,569,670

[45] Date of Patent: Oct. 29, 1996

[54] COMBINATION MEDICATIONS CONTAINING ALPHA-LIPOIC ACID AND RELATED

[75] Inventors: Carl-Heinrich Weischer, Bonn; Heinz Ulrich, Niedernberg; Klaus Wessel, Frankfurt, all of Germany

[73] Assignee: Asta Medica Aktiengesellschaft, Dresden, Germany

[21] Appl. No.: 404,153

[22] Filed: Mar. 14, 1995

Related U.S. Application Data

[60] Division of Ser. No. 197,643, Feb. 10, 1994, abandoned, which is a continuation-in-part of Ser. No. 71,259, Jun. 4, 1993, abandoned.

[30] Foreign Application Priority Data

Jun. 5, 1992 [DE] Germany ............ 42 185 72.6

[51] Int. Cl.⁶ .................................. A61K 31/385
[52] U.S. Cl. ............................ 514/440; 514/866
[58] Field of Search ............ 549/39, 35; 514/440, 514/866

[56] References Cited

U.S. PATENT DOCUMENTS

| | | | |
|---|---|---|---|
| 2,840,505 | 6/1958 | Grunert et al. | 549/30 |
| 2,933,430 | 4/1960 | Rosenberg | 549/30 |
| 3,049,549 | 8/1962 | Reed | 549/30 |
| 5,043,328 | 8/1991 | Weithmann | 514/78 |
| 5,084,481 | 1/1992 | Ulrich et al. | 514/557 |
| 5,118,505 | 6/1992 | Koltringer | 424/195.1 |
| 5,135,956 | 8/1992 | Borg et al. | 514/724 |
| 5,281,722 | 1/1994 | Blaschke et al. | 549/39 |
| 5,334,612 | 8/1994 | Kladen et al. | 514/440 |

FOREIGN PATENT DOCUMENTS 0184011  9/1985  Japan.

OTHER PUBLICATIONS

Chem. Abs. No. 108: 62485, "Hair Preparations containing throctu acid derivatives for dandruff control", Hasunma et al, 1988.

*Primary Examiner*—José G. Dees
*Assistant Examiner*—Deborah Lambkin
*Attorney, Agent, or Firm*—Cushman Darby & Cushman, LLP

[57] ABSTRACT

A pharmaceutical composition containing alpha-lipoic acid, dihydrolipoic acid, metabolites of alpha-lipoic acid (inter alia bisnortetralipoic acid and tetranorlipoic acid), optical isomers R- and S- forms of alpha-lipoic acid in oxidized and reduced form together with a vitamin, especially vitamins A, B1, B2, B6, B12, C and E and their pharmaceutically acceptable salts. The compositions are useful for producing analgesic, anti-inflammatory, antidiabetic, cytoprotective, anti-ulcer, antinecrotic, neuroprotective, detoxifying, anti-ischemic, liver function regulating, anti-allergic, immune-stimulating and antioncogenic effects.

1 Claim, No Drawings

COMBINATION MEDICATIONS CONTAINING ALPHA-LIPOIC ACID AND RELATED

This is a division of application Ser. No. 08/194,643, filed Feb. 10, 1994, now abandoned, which is a continuation in part of 08/071,259 filed Jun. 4, 1993, now abandoned.

The present invention relates to a synergistic combination of medications containing, as active ingredient, alpha-lipoic acid, dihydrolipoic acid, their metabolites as well as the oxidized and reduced enantionmers of alpha-lipoic acid such as R-alpha-lipoic acid or S-alpha-lipoic acid as well as metabolites of alpha-lipoic acid together with vitamins, especially vitamins A, B1–6, B12, C and E.

BACKGROUND OF THE INVENTION

Alpha-lipoic acid is 1,2-dithia-cyclopentane-3-valeric acid.

Alpha-lipoic acid is distributed widely in plants and animals in the form of the R-enantiomer; it acts as a coenzyme in many enzymatic reactions, constitutes a growth factor for certain bacteria and protozoa and is used to treat death-head mushroom poisoning. The alpha-lipoic acid racemate also has anti-inflammatory, antinociceptive (analgesic) and cytoprotective, neuroprotective, anti-allergic and antitumor properties.

The separated optical isomers of alpha-lipoic acid (R- and S-form, i.e. R-alpha-lipoic acid and S-alpha-lipoic acid), have different properties from each other and from the racemate. The R-enantionmer has a predominantly anti-inflammatory effect, and the S-enantiomer has a predominantly antinociceptive effect. The anti-inflammatory effect of the R-enantiomer is, for example, 10 times stronger than that of the racemate. The antinociceptive (analgesic) effect of the S-enantiomer is for example up to 6 times stronger than that of the racemate.

The enantiomers thus constitute very much more specific and stronger acting active substances as compared to the racemate.

These effects are described in Published European Patent Application EP-A 901213405.

Vitamin A is essential for growth, for bone development, normal function of the reproductive organs and the eyes and, above all, for the structure and function of mucous membrane epithelium.

Vitamin E essentially maintains the function of all cells, also those of the nervous system. Its main function is to protect lipids from peroxidation. Japanese published patent 3-193778 describes esters of lipoic acid with tocopherols. These tocopherol esters of lipoic acid are used to treat UV-erythemas.

Vitamin B1 is mainly active in thiamine deficiency syndrome, i.e. with severely deficient diet, long-term parenteral feeding, zero-diet, hemodialysis, malabsorption and alcohol abuse.

Vitamin B2 mainly acts in deficiency symptoms caused by alcohol abuse or insufficient intake of milk and milk products.

Vitamin B6 mainly acts in deficiency symptoms caused by alcohol abuse or chronic medication intake (oral contraceptives, isoniazid).

Vitamin B12 mainly acts in strict vegetarians, after gastric resection and atrophy of the mucous membrane or intestinal disorders which lead to deficiency symptoms such as anaemias, precipitations of the peripheral and central nervous system and polyneuropathies.

Vitamin C is part of the biochemical redox system and is involved in numerous electron transport reactions. These include, inter alia, collagen synthesis, noradrenaline, dopamine and serotinin synthesis and the degradation of 4-hydroxyphenyl-pyruvate. It also encourages the absorption of iron and has a stimulating effect on leucocyte phagocytosis activity. Together with carotinoids, vitamin A and E, vitamin C has been shown to have an antitumor effect.

SUMMARY OF THE INVENTION

The object of the present invention is to provide improved medications with analgesic, anti-inflammatory, antidiabetic, cytoprotective, anti-ulcer, antinecrotic, neuroprotective, detoxifying, heavy metal antidote, anti-ischemic, liver function regulating, anti-allergic, immune-stimulating and anti-oncogenic effect.

These and other objects are provided in medications which contain, as active ingredient, a member of the group consisting of alpha-lipoic acid, dihydrolipoic acid, their oxidized or reduced R- or S-isomers, and metabolites of alpha-lipoic acid (inter alia, 6,8-bisnorlipoic acid and tetranorlipoic acid), referred to hereinafter as "alpha-lipoic acid or related compound," and at least one vitamin or a pharmaceutically acceptable salt thereof. In a preferred form of the invention, the vitamin is selected from the group consisting of vitamins A, B1, B6, B12, C and E.

The tocopherols (vitamin E) used in the preparation according to this invention can be alpha-tocopherol, β-tocopherol, gamma-tocopherol or delta-tocopherol. These can be obtained from natural oils (d-form) as well as from synthetic material (dl-form). It is also possible to use tocopherol acetate as well as other esters of physiologically acceptable acids.

It has surprisingly been found that, in the combination of active substances, such as vitamin E, with the pure optical isomers of alpha-lipoic acid (R- and S-form, i.e. R-alpha-lipoic acid and S-alpha-lipoic acid), in contrast to the racemate of alpha-lipoic acid alone, the R-enantiomer has an anti-inflammatory and antidiabetic action, i.e. it reduces blood sugar, and the S-enantiomer has an antinociceptive effect in combination with vitamin E, the anti-inflammatory effect of the R-enantiomer in combination with vitamin E is surprisingly also stronger than that of the racemate of alpha-lipoic acid. The antinociceptive (analgesic) effect of the S-enantiomer in combination with vitamin E is for example stronger than that of the racemate of alpha-lipoic acid. The enantiomers in combination with vitamins A, B1, B2, B6, B12, C and E are therefore very much more specific and stronger acting active substances compared to the racemate of alpha-lipoic acid.

There are in particular the following differences compared to alpha-lipoic acid (racemate) in combination with vitamins A, B1, B2, B6, B12, C and E, such as the vitamins: in aqueous solutions the salts of the active compounds are preferably used with pharmaceutically acceptable salt formers. This means that the alpha-lipoic acid is not employed as the free acid in the pharmaceutical formulation, but it is employed as a salt with a pharmaceutically-acceptable salt former.

The preparation of alpha-lipoic acid, dihydrolipoic acid or of the oxidized or reduced R-alpha-lipoic acid and of S-alpha-lipoic acid or the metabolites of alpha-lipoic acid as well as their salts in combination with the vitamins listed is carried out in known manner, or by analogy thereto (See Published German Patent Application DE-OS 41 37 773).

Salt formers for alpha-lipoic acid, diydrolipoic acid, their oxidized or reduced R- or S-isomers, and metabolites of alpha-lipoic acid (6,8-bisnorlipoic acid and tetranorlipoic acid) can for example be conventional bases or cations which are physiologically acceptable in the salt form. Examples include: alkaline or alkaline earth metals, ammonium hydroxide, basic amino acids such as arginine and lysine, amines of formula $NR_1R_2R_3$ where the radicals $R_1$, $R_2$ and $R_3$ are the same or different and represent hydrogen, $C_1$–$C_4$-alkyl or $C_1$–$C_4$-oxyalkyl such as mono and diethanolamine, 1-amino-2-propanol, 3-amino-1-propanol; alkylene diamine with one alkylene chain composed of 2 to 6 carbon atoms such as ethylene diamine or hexamethylene tetramine, saturated cyclic amino compounds with 4–6 ring carbon atoms such as piperidine, piperazine, pyrrolidine, morpholine; N-methylglucamine, creatine and tromethamine.

RESULTS OF THE COMBINATIONS IN VARIOUS TEST MODELS

1) Analgesia

In the acetic acid writhing pain test in the mouse and the Randall Selitto inflammation pain test in the rat the S-enantiomer (S-alpha-lipoic acid) in the combination with vitamin E for example shows an analgesic effect which is superior to that of alpha-lipoic acid alone (i.e. the racemate) or of vitamin E alone (peroral administration).

2) Anti-inflammatory action

In carragheen-edema in the rat, the R-enantiomer (R-alpha-lipoic acid) in combination with vitamin E for example shows an anti-inflammatory effect which is superior to that of alpha-lipoic acid (alone) or to vitamin E alone (peroral administration).

3) Cytoprotective, antinecrotic and anti-ulcer effect

In addition, a cytoprotective effect is for example apparent in animal experiments both for the oxidized or reduced R- and S-form of alpha-lipoic acid in combination with vitamin E starting from a dose as low as 20 mg/kg R- and S-isomer of alpha-lipoic acid in combination with 50 mg/kg vitamin E per os.

4) Antidiabetic effect

In the alloxan diabetes model or the streptocytozine diabetes model the R-enantiomer (R-alpha-lipoic acid) in combination with vitamin E for example displays for example an antidiabetic, i.e. blood sugar-reducing effect, which is superior to that of alpha-lipoic acid (alone) or to vitamin E alone (peroral administration).

5) Liver metabolism regulating effect

In the rat, the R-enantiomer (R-alpha-lipoic acid) in combination with vitamin E displays for example a liver enzyme-regulating effect which is superior to that of alpha-lipoic acid (alone) or to vitamin E alone (peroral administration).

6) Detoxifying (heavy metal antidote) effect

In the heavy metal intoxication model in the rat, reduction in the heavy metal content in the liver, and thus a detoxifying effect, is for example present both for the oxidized or reduced racemates or R- and S-form of alpha-lipoic acid in combination with vitamin E from as low a dose as 30 mg/kg R- or S-isomer of alpha-lipoic acid in combination with 50 mg/kg vitamin E per os.

7) Immune stimulating effect

In cats infected with panleucopenia virus an immune stimulating effect occurs for example in animal experiments both for the oxidized or reduced R- and S-form of alpha-lipoic acid in combination with vitamin E from as low as dose as 35 mg/kg R- or S-isomer of alpha-lipoic acid in combination with 50 mg/kg vitamin E per os.

8) Growth-inhibiting effect on retroviruses

In addition, R- and S-alpha-lipoic acid in combination with vitamin E have a growth inhibiting effect against retroviruses, in particular the human immune deficiency virus HIV (HIV-1, HIV-2) and are therefore also suitable for the treatment of diseases caused by viruses of this type. They have a good, growth-inhibiting effect on HIV (types 1 and 2) which can for example be shown in vitro in the following virological-cell biological animal procedures:

1. Plaque reduction test
2. CPE reduction test
3. Determination of reverse transcriptase in the culture supernatant
4. Determination of p24 antigen in the culture supernatant Thus, for example, with a single administration of 0.035 mg/ml R- or S-isomer in combination with 0.1 mg/ml vitamin E the number of infectious viruses (for example HIV-1) in the cell culture supernatant is reduced from 100% in the positive control to 0%. A virus-inhibiting effect can be shown in this test at very low doses, for example 0.001 mg/ml.

As a general dose range for the effect (experiment as above) it is for example possible to use:

0.0035–0.091 mg/ml R- or S-isomer in combination with 0.001–0.01 mg/ml vitamin E, in particular 0.035–0.070 mg/ml R- or S-isomer in combination with 0.01–0.1 mg/ml vitamin E.

For the in vitro trials the active substance or the combination of active substances is for example used in benzyl alcohol as solvent.

For the in vitro investigations of the replication performance of retroviruses, in particular HIV, the following substrates can for example be used:

1. Virus-containing RPMI 1640 medium, for example 1X liquid 041-01875 (Gibco synthetic culture medium according to Moore, Gerner and Franklin, H. A. (1967), J.A.M.A. 199; 519) with a concentration of $2 \times 10^3$–$1 \times 10^3$ infectious units (PFU)/ml.
2. The cell lines Jurkat Clone E6-1, Sup T1 and HeLa CT4.

The combinations of alpha-lipoic acid, dihydrolipoic acid, their metabolites as well as the oxidized and reduced enantionmers of alpha-lipoic acid such as R-alpha-lipoic acid or S-alpha-lipoic acid as well as metabolites of alpha-lipoic acid with the vitamins A, B 1–6, B12, C and E display a good analgesic, anti-inflammatory, anti-arthrotic and cytoprotective effect in the following investigatory models:

$MgSO_4$ writhing test in the mouse after GYIRES et al. (Arch. int. pharmacodyn. therap. 267, 131–140, 1984) adjuvans-arthritis in the rat after NEWBOULD (Brit. J. Pharmacol. 21, 127–136, 1963) Na-monoiodacetate-induced arthrosis in rats and chickens according to KALBHEN in: Arthrosis deformans, Eular-Verlag, Basel/Switzerland, 1982; intestinal ulceration in rats after DEL SOLDATO (Agents and Actions 23, 1/2, 1988).

The combinations of these active substances show a cytoprotective, detoxifying effect in the following investigatory models: Examination of acute cell toxicity in mouse fibroblasts L 929 or the like after: LINDL et al. in: Zell und Gewebekultur, Gustav Fischer Verlag, Stuttgart, New York, 2nd edition, 1989, pages 164–167.

The combinations of these active substances show a good effect on metabolic activity in the following investigatory models: Examination of the influence of a substance on metabolic activity after: LINDL et al. in: Zell und Gewebekultur, Gustav Fischer Verlag, Stuttgart, New York, 2nd edition, 1989, pages 167–168.

The combinations of these active substances show a good growth-inhibiting effect in the following investigatory models: Examination of the growth-inhibiting properties of a substance using mouse fibroblasts (L929) or human fibroblasts (MRC9) after: LINDL et al. in: Zell und Gewebekultur, Gustav Fischer Verlag, Stuttgart, New York, 2nd edition, 1989, pages 162–164.

The combinations of these active substances show a good phagocyteosis-inhibiting effect in the following investigatory model in macrophages: Examination of the phagocytosis activity of macrophages after G. ROSSI, in: Zellkultur-Methoden, Berlin Oct. 7–9, 1987, Publ. H. R. Maurer, Inst. für Pharmazie der freien Universität Berlin, Sep. 29, 1987, page 163.

TOXICOLOGY OF THE COMBINATIONS COMPARED TO THE INDIVIDUAL ACTIVE SUBSTANCES

The acute toxicity of R-alpha-lipoic acid and S-alpha-lipoic acid in the mouse (expressed as the $LD_{50}$ mg/kg; LITCHFIELD and WILCOXON method, J. Pharmacol. Exp. Ther. 95, 99 (1949) ) is for example in excess of 1000 mg/kg with oral administration.

| TOXICITY | | |
|---|---|---|
| alpha-lipoic acid (racemate) | | |
| $LD_{50}$ | p.o.mg/kg | Species |
| | 502 | mouse, male |
| | 460 | mouse, female |
| | 1190 | rat, male |
| | 1210 | rat, female |

| TOXICITY | | | |
|---|---|---|---|
| Vitamin B1 | | | |
| $LD_{50}$ | p.o.mg/kg | i.v.mg/kg | Species |
| | 8200–13300 | 85–125 | mouse |
| | 12300 | 200–250 | rat |
| Vitamin B6 | | | |
| $LD_{50}$ | p.o.mg/kg | i.v.mg/kg | Species |
| | 8400 | 1020 | mouse |
| | 5500–15900 | 1450 | rat |
| Vitamin B12 | | | |
| $LD_{50}$ | p.o.mg/kg | | Species |
| | 1600 | | mouse |
| Vitamin C | | | |
| $LD_{50}$ | p.o.mg/kg | i.v.mg/kg | Species |
| | 8021 | 1058 | mouse |
| | >5000 | 1000 | rat |
| Vitamin E | | | |
| $LD_{50}$ | | | |
| | p.o.mg/kg | i.v.mg/kg | Species |
| | >50,000 | >2100 | mouse |
| | >5000 | >1500 | rat |

Examples: TOXICOLOGY OF THE COMBINATIONS
alpha-lipoic acid (racemate) with 30 mg/kg vitamin E
$LD_{50}$

| | p.o. | Species |
|---|---|---|
| | >1200 mg for alpha-lipoic acid | mouse |

Vitamin E (30 mg/kg p.o.) with R-enantiomer of alpha-lipoic acid
$LD_{50}$

| | p.o. | Species |
|---|---|---|
| | >1200 mg for the R-enantiomer of alpha-lipoic acid | mouse |

Vitamin E (30 mg/kg p.o.) with S-enantiomer of alpha-lipoic acid
$LD_{50}$

| | p.o. | Species |
|---|---|---|
| | >1200 mg for the S-enantiomer of alpha-lipoic acid | mouse |

PHARMACEUTICAL FORMULATIONS

The pharmaceutical formulations of the combination of the active substances, in accordance with the present invention, generally contain between 1 mg and 3 g as a single dose, preferably 2 mg to 1.2 g R- or S-alpha-lipoic acid for example in combination with 1 to 450 mg vitamin E. The active substance levels/kg body weight achieved should be between 1.5 and 200 mg for R- and S-alpha-lipoic acid, preferably between 4 and 100 mg, in particular between 8 and 70 mg/kg for the R- or S-form of alpha-lipoic acid and for example for the vitamin E preferably between 0.01 and 20 mg/kg BW, particularly between 0.1 and 8 mg/kg BW.

Administration can for example be in the form of tablets, capsules, pills, coated tablets, aerosols or in liquid form.

Liquid forms of administration that may for example be used are: alcoholic or aqueous solutions as well as suspensions and emulsions.

Preferred forms of administration are for example tablets containing between 10 mg and 2000 mg or solutions containing between 10 ml to 0.2 g/ml liquid of active substances.

TABLE 1

Example of oral doses to treat heavy metal intoxication in humans

| Alpha-lipoic acid or related compound | Vitamin | Daily Dose of Alpha-lipoic acid or related compound | Daily Dose of Vitamin | Single Dose of (a) Alpha-lipoic acid or related compound/ (b) Vitmain | Frequency of Administration (per day) |
| --- | --- | --- | --- | --- | --- |
| oxide/reduc. racemate or R- or S- isomer of alpha-lipoic acid | Vitamin A | 300 mg-1.2 g | 5,000-150,000 IU | (a) 100 mg-400 mg (b) 1,000 IU-30,000 | 1-4 |
| oxide/reduc. racemate or R- or S- isomer of alpha-lipoic acid | Vitamin B1 | 300 mg-1.2 g | 5-50 mg | (a) 100 mg-400 mg (b) 1 mg-12 mg | 1-4 |
| oxide/reduc. racemate or R- or S- isomer of alpha-lipoic acid | Vitamin B6 | 300 mg-1.2 g | 5-50 mg | (a) 100 mg-400 mg (b) 1 mg-12 mg | 1-4 |
| oxide/reduc. racemate or R- or S- isomer of alpha-lipoic acid | Vitamin B12 | 300 mg-1.2 g | 5-50 micrograms | (b) 1 microgram-12 micrograms a) 100 mg-400 mg | 1-4 |
| oxide/reduc. racemate or R- or S- isomer of alpha-lipoic acid | Vitamin C | 300 mg-1.2 g | 200-1,000 mg | (a) 100 mg-400 mg (b) 50 mg-250 mg | 1-4 |
| oxide/reduc. racemate or R- or S- isomer of alpha-lipoic acid | Vitamnin E | 250 mg-1.2 g | 100-800 mg | (a) 60 mg-400 mg (b) 25 mg-200 mg | 1-4 |

The single dose of active substance of the alpha lipoic acid or related compound in the combination for example with vitamin E can for example be:

a) in the oral medicinal form between 50 mg-3 g, preferably 100 mg-1.2 g.

b) in the parenteral medicinal form (for example intravenous, intramuscular) between 50 mg-2 g, preferably 100 mg -3 g.

c) in medicinal forms for inhalation (solutions or aerosols) between 100 micrograms-2 g, preferably 200 micrograms -1.2 g.

The doses according to a) to c) may for example be given 1 to 6 times, preferably 1 to 4 times daily or also as long-term infusion, for example with the aid of an infusionate.

The daily dose of R- or S-alpha-lipoic acid in the combination for example with vitamin E in man may for example be 2-40 mg per kg weight; the single dose for example 1-10 mg per kg weight, this dose appropriately being given up to 4 times daily.

The daily dose may for example be between 100-600 mg: the medications therefore preferably contain 100-600 mg of R- or S-alpha-lipoic acid in a pharmaceutical formulation, a dose of this kind preferably being given up to 4 times per day.

For treatment, it is for example possible to recommend 1 to 4 tablets, 3 times daily, with a content of 10 mg to 2 g alpha lipoic acid or related compound or for example in intravenous injection 1 to 4 times daily one ampoule/infusion vial of 1 to 100 ml content with 200 mg to 6 g alpha-lipoic acid or related compound in combination with 0.001-2 g of vitamin.

In oral administration, the minimum daily dose of the alpha lipoic acid or related compound in combination with the vitamin is for example 100 mg; the maximum daily dose in oral administration should not exceed 12 g.

The single dose of the vitamin in combination with the R- or S-isomer of alpha-lipoic acid can for example be, in the case of vitamin E:

a) in the oral medicinal form between 10 mg and 2 g, preferably 200-800 mg, in particular 25 mg-300 mg.

b) in the parenteral medicinal forms (for example intramuscular) between 0.1-25 mg/kg body weight, preferably 0.2-15 mg/kg body weight, in particular 1-190 mg/kg body weight.

c) in medicinal forms for inhalation (solutions or aerosols) between 0.01-15 mg/kg body weight, preferably 0.1 mg-10 mg/kg body weight, in particular 0.5-5 mg/kg body weight.

The doses according to a) to c) can for example be given 1 to 6 times, preferably 1 to 4 times daily.

The daily oral dose of vitamin E in combination with the oxidized or reduced racemate or R- or S-isomer of alpha-lipoic acid in man can for example be 0.1-12 mg/kg body weight; the single dose of vitamin E in the combination for example 0.1-25 mg per kg weight, this dose appropriately being given up to 4 times per day. The daily dose of vitamin E is preferably 200-800 mg: the medications therefore preferably contain 10-250 mg of vitamin E in a pharmaceutical formulation, a dose of this kind preferably being given 4 times.

For purposes of treatment it is for example possible to recommend for vitamin E in the combination 3 times daily 1 to 4 tablets containing 0.001 mg to 800 mg of the vitamin or for example in intravenous injection 1 to 4 times daily one ampoule/injection vial of 1 to 100 ml content with 0.10 mg to 200 mg vitamin.

In the case of oral administration the minimum daily dose for example of vitamin E in the combination is 50 mg; the maximum daily dose in oral administration should not exceed 1.5 g.

The medications of the invention can be used in human medicine alone or in a mixture with other pharmacologically active substances. The active substances R- or S-alpha-lipoic acid can also be combined with any other agent active against retroviruses, in particular HIV, for example didesoxyinosine, didesoxycytidine, however in particular with alpha-interferon and/or azidothymidine (AZT) or with cytostatics such as for example ifosfamide and endoxan.

The dose amounts cited of the alpha-lipoic acid or related compound always relate to the free acids of alpha-lipoic acid, dihydrolipoic acid or of oxidized or reduced R- or S-alpha-lipoic acid. Should these be used in the form of their salts, the stated dosages/dosage ranges should be correspondingly increased to the higher molecular weight.

In combinations with other antiretrovirally-effective substances (component b) only one, but also 2 and more (preferably 2) antiretrovirally active substances may be used as component b, in the latter case the dosages quoted for this purpose always apply to the sum of the antiretrovirally active substances in each case. The expression "dosage unit" always relates to a single dose which can also be administered several times per day.

Should the dose be quoted in the form of enzyme units, this is the dose which applies for an entire day, a dose of this kind being given once, preferably, however, distributed over one day (for example in infusion form). The dose information in enzyme units applies in particular to alpha-interferon.

It is for example possible for the combination of vitamin E with R- or S-alpha-lipoic acid with the component b for example AZT to mix the two components in each case for example in a ratio of 0.01 to 100 to 100 to 1 equimolar parts of active substance, in particular in a ratio of 1 to 10 to 10 to 1, preferably in a ratio of 0.1 to 3 up to 3 to 1 parts. In the case of a combination of vitamin E with R- or S-alpha-lipoic acid and alpha-interferon the three components may be present for example in the following ratios: 15 mg–50 mg–6 g R- or S-alpha-lipoic acid (component (a)) to $8\times10^6$ enzyme units to $1\times10^5$ enzyme units alpha-interferon, in particular 0.5–3 g component (a) to $1-4\times10^6$ enzyme units alpha-interferon. In the combination of for example vitamin E with R- or S-alpha-lipoic acid and other components according to b) both components may be present as a mixture. In general the components are however present separately from one another in a pharmaceutical formulation, it being possible to use conventional pharmaceutical formulations in this case: for example one component as a tablet or lacquered tablet, the other component as a powder, both in a capsule and vice versa, one component in the form of pellets, the other as a powder, coated tablet or tablets and vice versa and where the two forms are for example present in a capsule; or in the form of multi-layer or coated tablets. Reference is made in this connection for example to the book by Karl Thoma, Arzneimittelstabilität, Frankfurt 1978, for example page 207 et seq.

The combination of the invention may, however, also be present as a product in which in each case the two individual active substances are present in formulations totally separate from one another, it being possible in particular for the component (b), but also both components (a and b) to be contained in ampoules and/or infusion vials so that they can also be administered separately or also at different times.

Should such totally separate formulations be present, these are adapted to one another and contain the appropriate active substances in the dosage unit in the same amounts and corresponding weight ratios in which they can be present in the combined mixture.

In a product for separate administration it is also possible for both components not to be administered simultaneously. In such cases it is, for example, possible to give vitamin E intramuscularly and R- or S-alpha-lipoic acid as long-term infusion (dose for example 2–5 g per day) and the third component (b) simultaneously (dose for example 50–800 mg or $1-8\times10^6$ enzyme units, preferably intramuscular) or also as long-term infusion per day or R- or S-alpha-lipoic acid can for example be given 4 times daily (single dose for example 0.5–2 g) and the other component (b) simultaneously (dose for example 50–200 mg or $0.5-3\times10^6$ enzyme units), It is then for example possible for 1 to 3 further doses of component (b) (for example between 50–200 mg or $0.5-3\times10^6$ enzyme units) to follow at intervals of in each case 6 and/or 12 hours. The formulations/products of the invention can preferably also contain additional vitamins such as pantothenic acid and/or folic acid.

To treat diseases caused by retroviruses, in particular HIV viruses, appropriate medications should also contain such an amount of for example vitamin E in combination with R- or S-alpha-lipoic acid or these should be given in such amounts that single or multiple administration results in an active level of vitamin E in the body of between 0.001 and 12 mg/kg, preferably between 0.1 and 10 mg, in particular between 0.2 and 8 mg/kg body weight.

The general dose range for the combinations with the above mentioned vitamins with R- or S-alpha-lipoic acid for analgesic effect is for example: 0.5–20 mg/kg body weight oral vitamin E in combination with 1–100 mg/kg body weight R- or S-isomer of alpha-lipoic acid.

The general dose range of combinations with the above mentioned vitamins with R-alpha-lipoic acid for anti-inflammatory and cytoprotective effect is for example: 0.5–15 mg/kg body weight oral vitamin E in combination with 1–100 mg/kg body weight R- or S-isomer of alpha-lipoic acid The general dose range of combinations with the above mentioned vitamins with R-alpha-lipoic acid for the detoxifying, heavy metal antidote effect one can use for example: 0.5–25 mg/kg body weight oral vitamin E in combination with 1–100 mg/kg body weight R- or S-isomer of alpha-lipoic acid The general dose range of combinations with the above mentioned vitamins with R-alpha-lipoic acid for the anti-allergic and immune-stimulating effect one can use for example: 0.5–20 mg/kg body weight oral vitamin E in combination with 1–100 mg/kg body weight R- or S-isomer of alpha-lipoic acid The general dose range of combinations with the above mentioned vitamins with R-alpha-lipoic acid for the antitumor effect one can use for example: 0.5–25 mg/kg body weight oral vitamin E in combination with 1–100 mg/kg body weight R- or S-isomer of alpha-lipoic acid The general dose range of combinations with the above mentioned vitamins with R-alpha-lipoic acid for the antidiabetic effect one can use for example: 0.5–20 mg/kg body weight oral vitamin E in combination with 1–100 mg/kg body weight R- or S-isomer of alpha-lipoic acid The following indications may for example be considered: inflammatory, degenerative articular and extra-articular rheumatic disorders, non-rheumatic inflammations and swellings, Arthrosis deformans, chondropathies, periarthritis, inflammatory and non-inflammatory diseases of the skin, such as neurodermitis and psoriasis, inflammatory and non-inflammatory disorders of the gastrointestinal tract, such as gastritis, Ulcus ventriculi, ileitis, duodenitis, infections with Campylobacter pylorici, jejunitis, colitis, diabetes mellitus Types I and II, insulin resistance, polyneuropathy of diabetogenic, alcoholic, hepatic and uremic origin, liver parenchyme degeneration, hepatitis, fatty liver and fatty cirrhosis, heavy metal poisonings such as copper, zinc, cadmium, nickel, lead and arsenic as well as radioactive isotope intoxication as well as chronic liver diseases, inflammatory respiratory tract diseases, such as Asthma bronchiale, sarcoidosis, ARDS (acute respiratory distress syndrome), degenerative diseases of the CNS, acute ischemic states, myocardial infarction, kidney parenchyme degeneration.

In accordance with the invention, the dosage forms of the combinations for the analgesic heavy metal antidote, detoxifying, antidiabetic, immune-stimulating and cytoprotective, antinecrotic and/or anti-inflammatory effect are for example 0.01 to 800 mg vitamin E, preferably 0.1 to 600 mg vitamin E in combination with 0.1 to 2000 mg, preferably 15 to 600 mg and in particular 50 to 200 mg R-alpha-lipoic acid or S-alpha-lipoic acid.

In accordance with the invention, a daily dose of the combinations of the above named vitamins with the optical isomers of alpha-lipoic acid (R- or S-form) can be from 0.1 to 800 mg vitamin E, preferably 1 to 600 mg vitamin E in combination with the optical isomers of alpha-lipoic acid (R- or S-form in each case) 10–600 mg, preferably 25 to 400 mg or 10 to 200 mg. The maximum daily dose for the cytoprotective effect and for the treatment of states of pain and inflammation should not exceed 1.2 g for the racemate -or R- or S-form of alpha-lipoic acid and 800 mg for vitamin E. The daily doses may be used in the form of a single administration of the entire amount or in the form of 1 to 6, in particular 1–4 partial doses per day.

In general administration of 1 to 4 times, in particular 1 to 3 times daily is preferred.

For example, the preferred daily dose in the combination with vitamin E (0.1–800 mg for the oral administration of vitamin E in the combination and 0.1–20 mg/kg for the intramuscular administration of vitamin E in the combination) both for R-alpha-lipoic acid and also for S-alpha-lipoic acid is preferably 100 mg for the parenteral form of administration and 400 mg for the oral form.

For example the daily dose for the parenteral form of administration of the R- or S-isomers of alpha-lipoic acid in the combination with the vitamin can in particular be 300 mg and 600 mg for the oral form.

The medications are preferably given orally. For example, the vitamin E in the combination with R-alpha-lipoic acid and S-alpha-lipoic acid can in particular also be administered in the form of a solution, for example peroral, topical, parenteral (intravenous, intra-articular, intramuscular, subcutaneous), inhalative, transdermal. The medications containing as active substance for example vitamin E in combination with R-alpha-lipoic acid or S-alpha-lipoic acid can for example be formulated in the form of tablets, capsules, pills or coated tablets, granulates, pellets, plasters, solutions or emulsions, the active substances in each case optionally being combined with appropriate auxiliary substances and carriers. In the case of solutions in each case of 10–600 mg, for example from 25 to 400 mg or 10 to 200 mg administered. The maximum daily dose for the antidiabetic, immune-stimulating, anti-allergic, cytoprotective effect and for the treatment of pain and inflammatory states should for example for the combination of vitamin E with the R- or S-isomers of alpha-lipoic acid for the vitamin E not exceed 800 mg orally and for the R- and S-isomers of alpha-lipoic acid 1.2 g.

The maximum daily dose for the detoxifying, heavy metal antidote effect should for example for the combination of vitamin E with the R- or S-isomers of alpha-lipoic acid for the vitamin E not exceed 1200 mg orally and 1200 mg for the R- or S-isomers of alpha-lipoic acid.

The daily doses can be used in the form of a single administration of the entire amount or in the form of 1 to 6, in particular 1–4 partial doses per day. In general an administration of 1 to 4 times, in particular 1 to 3 times daily is preferred.

The preferred daily dose in the combination both for the vitamin E is for example 800 mg orally, preferably 600 mg oral and parenteral for vitamin E 15 mg/kg body weight intramuscular and for R-alpha-lipoic acid and also for S-alpha-lipoic acid preferably 80 mg for the parenteral form of administration and 200 mg for the oral form.

The R-alpha-lipoic acid and S-alpha-lipoic acid in the combination with for example vitamin E can for example also be administered in particular in the form of a solution, for example peroral, topical, parenteral (intravenous, intra-articular, intramuscular, subcutaneous), inhalative, transdermal. Medicaments containing as active substances for example vitamin E in the combination with R-alpha-lipoic acid or S-alpha-lipoic acid can for example be formulated in the form of tablets, capsules, pills or coated tablets, granulates, pellets, plasters, solutions or emulsions, where the active substance is in each case optionally combined with appropriate auxiliary substances and carriers. In the case of solutions these contain for example 0.5 to 20 weight %, preferably 1 to 10 weight % of one of the optical isomers of alpha-lipoic acid (in each case R-form or S-form) together with 0.001 to 10 weight % of the appropriate vitamin.

The dosage unit of medications with for example vitamin E in combination with the optical isomers of alpha-lipoic acid or a therapeutically acceptable salt thereof (R-form or S-form in each case) can for example contain:

a) in the case of oral medications: 10 to 1200 mg, preferably 20 to 600 mg, in particular 50 to 400 mg of the optical isomers of alpha-lipoic acid in combination with for example vitamin E 0.1 to 800 mg, preferably 1 to 400 mg, in particular 1–300 mg.

The doses can for example be given 1 to 6 times, preferably 1 to 4 times, in particular 1 to 3 times daily. However a total dose of the optical isomers of alpha-lipoic acid of 1200 mg and for example of vitamin E of 800 mg per day should not be exceeded for the cyto-protective effect and for the treatment of states of pain and inflammation. The same also applies to the following medicinal forms listed under b) to e). In addition a total dose of the optical R- or S-isomers of alpha-lipoic acid of 2000 mg and for example of vitamin E of 1200 mg per day should not be exceeded for the detoxifying and heavy metal antidote effect.

b) in the case of parenteral medicinal forms (for example intravenous, intramuscular or intra-articular), 10 to 600 mg, preferably 15 to 500 mg, in particular 20 to 300 mg of the optical isomers of alpha-lipoic acid in the combination for example with vitamin E 0.01–20 mg/kg body weight intramuscular, preferably 0.1–12 mg/kg body weight in particular 1–10 mg/kg body weight intramuscular.

The doses can for example be administered 1 to 6 times, preferably 1 to 4 times, in particular 1 to 3 times daily.

c) in the case of medicinal forms for application to the skin and mucous membranes (for example as solutions, lotions, emulsions, ointments, plasters and the like) in the combination: 10 to 500 mg R-alpha-lipoic acid or S-alpha-lipoic 15 acid, preferably 40 to 250 mg, in particular 50 to 200 mg with for example the combination partner vitamin E 0.1–600 mg, preferably 1–400 mg, in particular 5–200 mg. These doses can for example be given 1 to 6 times, preferably 1 to 4 times, in particular 1 to 3 times daily.

d) in the case of medicinal forms for inhalation (solutions or aerosols): 0.07 to 300 mg, preferably 0.25 to 150 mg, in particular 0.5 to 80 mg R-alpha-lipoic acid or S-alpha-lipoic acid combination with for example vitamin E preferably 0.001–20 mg/kg, in particular 0.01 to 10 mg/kg. These doses may for example be administered 1 to 6 times, preferably 1 to 4 times, in particular 1 to 3 times daily.

If solutions are used, the optical isomers of alpha-lipoic acid and the vitamins contained in the combination are preferably used in the form of a salt.

It is of course also possible to prepare pharmaceutical formulations .which contain 2 up to for example 6 times the above stated dosage units. In particular tablets or capsules contain 20 to 800 mg of the alpha-lipoic acid or related compound in combination with a vitamin, for example vitamin E 1–1200 mg, pellets, powders or granulates 20 to 400 mg of the alpha-lipoic acid or related compound in combination with a vitamin, for example vitamin E 1–800 mg, suppositories 20 to 300 mg of alpha lipoic acid or related compound in combination with a vitamin, for example 1–600 mg of vitamin E R-alpha-lipoic acid or S-alpha-lipoic acid.

To combat retroviruses (for example AIDS) the daily dose is for example 4–6 g R- or S-isomer of alpha-lipoic acid in the combination with for example vitamin E 1–1200 mg.

Corresponding medications consequently preferably contain in the combination with 5 mg–1 g vitamin E, R-alpha-lipoic acid or S-alpha-lipoic acid in the single dose (dosage unit) for example in an amount of 600 mg to 1.5 g.

The above stated dosages always relate to combinations with the cited vitamins with, for example, the free optical isomers of alpha-lipoic acid. If the optical isomers of alpha-lipoic acid are used in the form of a salt, the stated dosages/dosage ranges should be increased accordingly on account of the higher molecular weight.

In the event of the combination with the vitamins such as for example vitamin E being used with the optical isomers of alpha-lipoic acid in animals, the following indications may in particular be considered: panleucopenia, distemper, hepatoses, Arthrosis deformans, arthritis and dermatitis.

For the treatment of animals, it is for example possible to use the following dosages (vitamin E both in combination with the R-form and with the S-form of alpha-lipoic acid):

For the treatment of cats, the oral single dose is generally between about 2 mg/kg and 50 mg/kg of the alpha-lipoic acid or related compound, in combination for example with vitamin E, 0.1 to 100 mg/kg, preferably 1 to 80 mg/kg, in particular 2–40 mg/kg body weight, the parenteral dose is between 0.5 and 40 mg/kg body weight of alpha lipoic acid or related compound in combination with the vitamin for example vitamin E 0.01 mg/kg to 10 mg/kg, preferably 0.1 to 8 mg/kg, in particular 1–4 mg/kg.

For the treatment of arthroses in horses and cattle, the oral single dose in general in the combination for the alpha-lipoic acid or related compound is between about 2 mg/kg and 100 mg/kg body weight and for the vitamin between about 2 mg/kg and 100 mg/kg body weight, the parenteral dose in the combination for the alpha-lipoic acid or related compound is about between 0.5 and 50 mg/kg body weight and for the vitamin about between 0.005 and 20 mg/kg body weight.

The vitamin and alpha-lipoic acid or related compound such as the optical isomers of alpha-lipoic acid are suitable for the preparation of pharmaceutical compositions and formulations. The pharmaceutical compositions or medications contain for example the optical isomers of alpha-lipoic acid as active substance, optionally in a mixture with the vitamin or other pharmacological or pharmaceutically active substances. The medications are prepared in known manner, it also being possible to use known and conventional pharmaceutical auxiliary substances as well as other conventional carriers and diluting agents. Carriers and auxiliary substances that may for example be considered are those recommended or quoted in the following literature references as auxiliary substances for use in pharmaceuticals, cosmetics and related fields:

Ullmanns Enzyklopadie der technischen Chemie, Volume 4 (1953), page 1 to 39; Journal of Pharmaceutical Sciences, Volume 52 (1963), page 918 et seq., H. v. Czetsch-Lindenwald, Hilfsstoffe für Pharmazie und angrenzende Gebiete; Pharm. Ind., Issue 2 (1961), page72 et seq., Dr. H. P. Fiedler, Lexikon der Hilfsstoffe für Pharmazie, Kosmetik und angrenzende Gebiete, Cantor KG, Aulendorf in Württemberg (1989).

The pharmaceutical and galenic handling of the vitamins and of the alpha lipoic acid or related compounds such as for example R- or S-alpha-lipoic acid is effected using conventional standard methods.

For example in 1 to 5 ml vitamin E, for example 250 mg dihydrolipoic acid, or in 10 ml vitamin E, for example 250 mg R-alpha or S-alpha-lipoic acid, and/or auxiliary or carrier substances are well mixed by stirring or homogenizing (for example using conventional mixing apparatus) (clear solution), the operation being carried out generally at temperatures between 20° and 50° C., preferably 20° to 40° C., in particular at room temperature. Reference is also made to the following standard textbook: Sucker, Fuchs, Speiser, Pharmazeutische Technologie, Thieme-Verlag Stuttgart, 1978.

Administration of the vitamin with the alpha-lipoic acid or related compound, such as for example R- or S-alpha-lipoic acid, or of the medications can be to the skin or mucous membrane or to the inside of the body, for example oral, enteral, pulmonal, nasal, lingual, intravenous, intraarterial, intracardial, intramuscular, intraperitoneal, intracutaneous, subcutaneous.

The parenteral formulation forms are in particular sterile or sterilized products.

If, for example, the vitamin E is used in combination with R- or S- alpha-lipoic-acid in the form of their salts, the salt formers can also be used in excess, that is in a higher amount than equimolar.

Examples of carriers and auxiliary substances are gelatin, natural sugars such as cane sugar or lactose, lecithin, pectin, starches (for example corn starch or amyloses), cyclodextrins and cyclodextrin derivatives, dextran, polyvinyl pyrrloidone, polyvinyl acetate, gum arabic, alginic acid, tylose, talcum, lycopodium, silica (for example colloidal silica), cellulose, cellulose derivatives (for example cellulose ethers in which the celluosic hydroxy groups are partially etherified with lower saturated aliphatic alcohols and/or lower saturated aliphatic oxyalcohols, for example methyloxypropyl cellulose, methyl cellulose, hydroxypropyl methyl cellulose, hydroxypropyl methyl cellulose phthalate, fatty acids as well as magnesium, calcium or aluminum salts of fatty acids with 12 to 22 carbon atoms, in particular saturated (for example stearates), emulsifiers, oils and fats, in particular vegetable (for example peanut oil, castor oil, olive oil, sesame oil, cotton seed oil, corn oil, wheat germ oil, sunflower seed oil, cod liver oil, in each case also hydrated); glycerol esters and polyglycerol esters of saturated fatty acids of the formula $C_{12}H_{24}O_2$ to $C_{18}H_{36}O_2$ and their mixtures, where the glycerol-hydroxy groups are totally or also only partially esterified (for example mono, di and triglycerides), pharmaceutically acceptable mono or multivalent alcohols and polyglycols such as polyethylene glycols (molecular weight range for example 300 to 1500) as well as derivatives thereof, polyethylene oxide, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycolen, glycerol, diethylene glycol, pentaerythritol, sorbitol, mannitol and the like, which may optionally also be etherified, esters of citric acid with primary alcohols, acetic acid, urea, benzyl benzoate, dioxolanes, glyzerol formals, tetrahydrofurfuryl alcohol, polyglycolesters with $C_1$–$C_{12}$- alcohols, dimethylacetamide, lactamides, lactates, ethylcarbonates, silicones (in particular medium-viscous polydimethylsiloxanes), calcium carbonate, sodium carbonate, calcium phosphate, sodium phosphate, magnesium carbonate and the like. Other auxiliary substances that may be considered are substances which effect disintegration (so-called disintegrants) such as cross-linked polyvinyl pyrrolidone, sodiumcarboxymethyl starches, sodiumcarboxymethyl cellulose or microcrystalline cellulose. It is also possible to use known coating materials. Agents of this type that may for example be used are:

Polymers as well as copolymers of acrylic acid and/or methacrylic acid and/or their esters, copolymerisates of acrylic and methacrylic acid esters with a lower ammonium group content (for example Eudragit® RS), copolymers of acrylic and methacrylic acid esters and trimethylammonium methacrylate (for example Eudragit® RL); polyvinylacetate; fats, oils, waxes, fatty alcohols;

hydroxypropyl methyl cellulose phthalate or -acetate succinate; cellulose acetate phthalate, starch acetate phthalate as well as polyvinylacetate phthalate; carboxymethyl cellulose; methyl cellulose phthalate, methyl cellulose succinate, -phthalate succinate as well as methyl cellulose phthalic acid half esters; zein; ethyl cellulose as well as ethyl cellulose succinate; shellac, gluten; ethylcarboxyethyl cellulose; ethacrylate maleic acid anhydride copolymer; maleic acid anhydride vinylmethylether copolymer; styrolmaleic acid copolymers; 2-ethyl-hexyl-acrylate maleic acid anhydride; crotonic acid-vinyl acetate copolymer;

glutaminic acid/glutaminic acid ester-copolymer; carboxymethylethyl cellulose glycerol mono-octanoate; celluloseacetate succinate; polyarginine.

Plasticizing agents for coatings that may be used are:

citric and tartaric acid esters (acetyltriethyl citrate, acetyltributyl-, tributyl-, triethyl citrate); glycerol and glycerol esters (glycerol diacetate, - triacetate, acetylated monoglycerides, castor oil); phthalic acid esters (dibutyl-, diamyl-, diethyl-, dimethyl, dipropyl-phthalate, di-(2-methoxy- or 2-ethoxyethyl)-phthalate, ethylphthalylglycolate, butylphthalyl ethylglycolate and butylglycolate; alcohols (propylene glycol, polyethylene glycol of various chain lengths), adipates (diethyladipate, di-(2-methoxy- or 2-ethoxyethyl)-adipate); benzophenone; diethyl- and dibutylsebacate, dibutylsuccinate, dibutyltartrate; diethyleneglycol dipropionate; ethylene glycoldiacetate, -dibutyrate, -dipropionate, tributylphosphate, -tributyrin, polyethylene glycol sorbitan monooleate (polysorbates such as polysorbate 80); sorbitan monooleate.

For the preparation of solutions or suspensions it is for example possible to use water or physiologically acceptable organic solvents such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil), paraffins, dimethylsulfoxide, triglycerides and the like. For injectable solutions or suspensions it is for example possible to use non-toxic parenterally acceptable dissolution agents or solvents, such as: water, 1,3-butane diol, ethanol, 1,2-propylene glycol, polyglycols mixed with water, glycerol, Ringer's solution, isotonic sodium chloride solution or also solidified oils including synthetic mono- or diglycerides or fatty acids such as oleic acid.

To prepare the formulations it is possible to use known and conventional solubilizers or emulsifiers. Solubilizers and emulsifiers that may for example be used are: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, -linolizated oleotriglycerides, polyethylene oxide condensation products of fatty alcohols, alkyl phenols or fatty acids or also 1-methyl-3-(2-hydroxyethyl) imidazolidone-(2).

In this context, polyoxyethylated means that the appropriate substances contain polyoxyethylene chains, the degree of polymerization of which generally lies between 2 and 40, and in particular between 10 to 20. Polyoxyethylated substances of this type may for example be obtained by reacting hydroxyl group-containing compounds (for example mono- or diglycerides or unsaturated compounds such as those containing oleic acid radicals) with ethylene oxide (for example 40 mol ethylene oxide per 1 mol glyceride). Examples of oleotriglycerides are olive oil, peanut oil, castor oil, sesame oil, cotton seed oil, corn oil.

See also Dr. H. P. Fiedler "Lexikon der Hilfsstoffe für Pharmazie, Kosmetik und angrenzende Gebiete" 1971, p. 191–195.

In addition it is also possible to add preservatives, stabilizers, buffers, flavor correcting agents, sweeteners, colorants, antioxidants, complex formers and the like. Complex formers that may for example be considered are: chelate formers such as ethylenediamino tetraacetic acid, nitrilotriacetic acid, diethylene triamine pentaacetic acid as well as their salts. It is also possible to use as complex formers those containing the vitamin in combination with for example R- or S-alpha-lipoic acid in a cavity.

Examples are urea, thiourea, cyclodextrins, amylose. It is optionally necessary to stabilize the active substance molecule with physiologically acceptable bases or buffers to a pH range of approx 6 to 9. In general as neutral to weakly basic (up to pH 8) a pH value as possible is preferred.

Antioxidants that may for example be used are sodium sulfite, sodium hydrogen sulfite, sodium metabisulfite, ascorbic acid, ascorbyl palmitate, -myristate, -stearate, gallic acid, gallic acid alkyl ester, butylhydroxyanisol, nordihydroguaiacic acid, tocopherols as well as synergists (substances which form heavy metals through complex formation, for example lecithin, ascorbic acid, phosphoric acid ethylene diamine tetraacetic acid, citrates, tartrates). The addition of synergists considerably raises the antioxygenic effect of the antioxidants.

Preservatives that may for example be used are sorbic acid, p-hydroxybenzoic acid ester (for example lower alkyl ester), benzoic acid, sodium benzoate, trichloroisobutyl alcohol, phenol, cresol, benzethonium chloride, chlorohexidine and formalin derivatives.

SPECIFIC EXAMPLES OF PREFERRED EMBODIMENTS

The invention is illustrated by the following examples:

EXAMPLE 1

Suppositories with 50 mg dihydrolipoic acid or with R- or S-alpha-lipoic acid and 200 mg alphatocopherol or 200 mg alphatocopherol acetate 5 g ascorbyl palmirate and 5 g Oxynex LM**) (E. Merck, Darmstadt) are suspended in 175 g molten hard fat*). 20 g alpha tocopherol and 5 g dihydrolipoic acid are then added thereto and the mixture is cast into hollow cells of 2.3 ml after homogenization and cooled. Before sealing the hollow cells are flushed with nitrogen.

*) hard fat is a mixture of mono-, di- and triglycerides of saturated fatty acids having the formula $C_{10}H_{20}O_2$ to $C_{18}H_{36}O_2$
**) Oxynex LM is a commercial additive for fats and fat-containing foodstuffs. It is a light brown to brown, waxy mass which melts on heating to 55° C. to a clear brown liquid and contains tocopherol, ascorbyl palmirate, citric acid and lecithin.

Each suppository weighing 2.1 g contains 50 mg dihydrolipoic acid and 200 mg alphatocopherol.

Suppositories with R- or S-alpha-lipoic acid may be prepared in the same manner by using the same amount of either R- or S-alpha-lipoic acid instead of dihydrolipoic acid.

EXAMPLE 2

Capsules containing 200 mg dihydrolipoic acid or R- or S-alpha-lipoic acid and 500 mg alphatocopherol or alphatocopherol acetate 200 g R-alpha-lipoic acid are mixed with 500 g alphatocopherol. 595 g Miglyol® *) neutral oil and 100 g sorbitol syrup, 25 g glycerol are then added thereto and the mixture filled into size 00 capsules. Each capsule weighing 1.42 g contains 200 mg R- or S-alpha-lipoic acid and 500 mg alphatocopherol.

*) Miglyol® is a commercial mixture of medium-chain triglycerides

In the same manner it is possible to prepare capsules with dihydrolipoic acid or with S-alpha-lipoic acid by using the same amount of either dihydrolipoic acid or S-alphalipoic acid instead of R-alpha-lipoic acid.

EXAMPLE 3

Ampoules containing 250 mg R- or S-alpha-lipoic acid and 250 mg vitamin C (ascorbic acid) in 10 ml 250 g R-alpha-lipoic acid are dissolved with stirring together with 352.3 tromethamine (2-amino-(hydroxymethyl)-1,3-propanediol) in a mixture of 8 liters of water sterilized for injection purposes and 200 g 1,2-propylene glycol with stirring. 250 mg vitamin C are then dissolved into this batch. The solution is made up to 10 liters with water sterilized for injection purposes and then filtered through a membrane filter of pore size 0.2 µm with glass fiber prefilter. The filtrate is filled under aseptic conditions in 10 ml portions into sterilized 10 ml ampoules.

Each ampoule contains 250 ml R-alpha-lipoic acid as tromethamine salt and 250 mg vitamin C in 10 ml injection solution.

In the same manner it is possible to prepare ampoules with S-alpha-lipoic acid by using the same amount of S-alpha-lipoic acid instead of R-alpha-lipoic acid.

EXAMPLE 4

Tablets with 50 mg S- or R-alpha-lipoic acid and 50 mg vitamin C ascorbic acid 250 g S-alpha-lipoic acid and 250 g vitamin C are evenly ground with 550 g microcrystalline cellulose. After sieving the mixture, 250 g starch (starch 1500/Colorcon), 682.5 g lactose, 15 g magnesium stearate and 2.5 g highly disperse silicon dioxide are added thereto and the mixture is pressed into tablets weighing 400.0 mg each.

Each tablet contains 50 mg S-alpha-lipoic acid and 50 mg vitamin C.

In the same manner it is possible to prepare tablets with 50 mg R-alpha-lipoic acid by using the same amount of R-alpha-lipoic acid instead of 250 g S-alpha-lipoic acid.

The tablets may optionally be provided with a gastric juice soluble or gastric juice permeable film coating using conventional methods.

EXAMPLE 5

Ampoules containing 50 mg dihydrolipoic acid or 50 mg R- or S-alpha-lipoic acid and 200 mg alphatocopherol acetate in 4 ml injection solution 50 g R-alpha-lipoic acid are dissolved with 750 g alphatocopherol acetate. The solution is diluted with 3200 g neutral oil.

The solution is sterilized Using gamma or beta radiation and filled in 10 ml portions into sterilized 10 ml ampoules under aseptic conditions. Each 10 ml ampoule contains 50 mg R-alpha-lipoic acid and 200 mg alphatocopherol acetate.

In the same manner it is possible to prepare ampoules with dihydrolipoic acid or with S-alpha-lipoic acid by using the same amount of either dihydrolipoic acid or S-alpha-lipoic acid instead of R-alpha-lipoic acid.

EXAMPLE 6

Ointment with 2% dihydrolipoic acid or 2% R- or S-alpha-lipoic acid and with 2% alphatocopherol 20 g R-alpha-lipoic acid are mixed with 20 g alphatocopherol with 400 g Vaselinum album and 100 g sorbitol 70% and 100 g Alcohol cetylicus et stearylicus and 360 g wool wax.

This mixture is filled under sterile conditions into 50 g tubes after homogenization.

The ointment contains 2% R-alpha-lipoic acid and 2% alphatocopherol acetate.

In the same manner it is possible to prepare an ointment with dihydrolipoic acid or with S-alpha-lipoic acid by using the same amount of either dihydrolipoic acid-or S-alpha-lipoic acid instead of R-alpha-lipoic acid.

EXAMPLE 7

Tablets containing 120 mg S- or R-alpha-lipoic acid and 61 mg vitamin C ascorbic acid 825 g S-alpha-lipoic acid and 425 g vitamin C are evenly ground with 550 g microcrystalline cellulose. After the mixture has been sieved, 250 g starch (starch 1500/Colorcon), 682.5 g lactose, 15 g magnesium stearate and 2.5 g highly disperse silicon dioxide are added and the mixture is pressed into tablets weighing 400.0 mg each.

Each tablet contains 120 mg S-alpha-lipoic acid and 61 mg vitamin C.

In the same manner it is possible to prepare tablets with 120 mg R-alpha-lipoic acid by using the same amount of R-alpha-lipoic acid instead of S-alpha-lipoic acid.

The tablets may optionally be provided with a gastric juice soluble or gastric juice permeable film coating using conventional methods.

What is claimed is:

1. A method of treating diabetes mellitus Type I or Type II which comprises administering to a mammal having diabetes mellitus Type I or Type II a therapeutically effective amount of a composition comprising pure R-alpha-lipoic acid and vitamin E, or a pharmaceutically acceptable salt thereof.

* * * * *